United States Patent
Bahls et al.

(10) Patent No.: US 9,216,032 B2
(45) Date of Patent: Dec. 22, 2015

(54) LIQUID JET SCALPEL AND METHOD FOR OPERATING A LIQUID JET SCALPEL

(71) Applicant: Deutsches Zentrum fuer Luft- und Raumfahrt e.V., Cologne (DE)

(72) Inventors: Thomas Bahls, Weil (DE); Florian Alexander Froehlich, Germering (DE)

(73) Assignee: Deutsches Zentrum für Luft- und Raumfahrt e.V., Cologne (DE)

( * ) Notice: Subject to any disclaimer, the term of this patent is extended or adjusted under 35 U.S.C. 154(b) by 158 days.

(21) Appl. No.: 13/705,623

(22) Filed: Dec. 5, 2012

(65) Prior Publication Data
US 2013/0172916 A1    Jul. 4, 2013

Related U.S. Application Data

(60) Provisional application No. 61/711,881, filed on Oct. 10, 2012.

(30) Foreign Application Priority Data
Dec. 5, 2011   (DE) .......................... 10 2011 087 748

(51) Int. Cl.
*A61B 17/3203* (2006.01)
*A61B 19/00* (2006.01)

(52) U.S. Cl.
CPC ......... *A61B 17/3203* (2013.01); *A61B 19/5244* (2013.01); *A61B 2019/461* (2013.01)

(58) Field of Classification Search
CPC ........... A61B 17/3205; A61B 17/3203; A61B 207/320052; A61B 19/46; A61B 19/50; A61B 2019/461; A61B 2019/5244; A61B 2019/5246; A61B 2019/5248; A61B 2019/5251; A61B 2019/5268; A61B 2019/501; A61B 2019/504; A61B 2019/507; A61B 2019/5255; A61B 2018/202; A61B 18/20; G01B 11/16; G01B 11/002; G01B 11/14; G01B 9/02; G06F 3/0346; G06F 3/0425
USPC .................. 606/167, 170, 159, 169, 130, 45; 604/22, 70, 21; 73/1.05, 504.06, 700, 73/703, 504.01–504.03; 417/151, 417/178–180, 182, 184; 440/38–40, 47; 239/698, 704, 697, 399, 402.5, 403, 239/404, 406–408
See application file for complete search history.

(56) References Cited

U.S. PATENT DOCUMENTS

| 7,657,101 B2* | 2/2010 | Christiansen et al. ........ 382/218 |
| 2004/0059216 A1* | 3/2004 | Vetter et al. .................. 600/424 |

(Continued)

FOREIGN PATENT DOCUMENTS

| DE | 102 40 654 A1 | 3/2004 |
| DE | 10237945 A1 | 3/2004 |
| WO | 02/34153 A1 | 5/2002 |
| WO | 2011/141775 | 11/2011 |

OTHER PUBLICATIONS

European Search Report for corresponding European Application No. 12194039.9 dated Feb. 1, 2013.

(Continued)

*Primary Examiner* — Jocelin Tanner
(74) *Attorney, Agent, or Firm* — Renner, Otto, Boisselle & Sklar, LLP

(57) ABSTRACT

The invention relates to a liquid jet scalpel comprising a nozzle (12) for discharge of pressurized liquid (14) in the direction of tissue (16) that is to be manipulated, and a distance measuring device (18) for measuring the distance between the nozzle (12) and the tissue (16) that is to be manipulated.

The invention further relates to a method for operating a liquid jet scalpel.

6 Claims, 1 Drawing Sheet

(56) References Cited

U.S. PATENT DOCUMENTS

| | | |
|---|---|---|
| 2006/0100612 A1 | 5/2006 | Van der Heyd et al. |
| 2007/0255169 A1 | 11/2007 | Hashimshony et al. |
| 2009/0227998 A1* | 9/2009 | Aljuri et al. ............ 606/13 |
| 2010/0082053 A1 | 4/2010 | Hama et al. |
| 2010/0256504 A1 | 10/2010 | Moreau-Gaudry et al. |
| 2010/0324366 A1* | 12/2010 | Shimotsu ............ 600/109 |
| 2011/0208256 A1* | 8/2011 | Zuhars ............ 606/86 R |

OTHER PUBLICATIONS

Zheng, Y P et al.; "Ultrasound elastomicroscopy using water jet and osmosis loading: Potentials for assessment for articular cartilage", 2006.

* cited by examiner

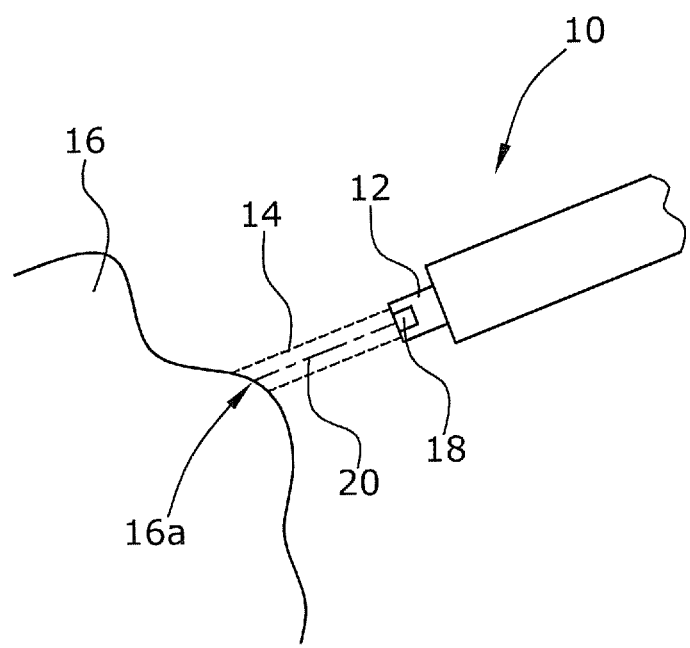

LIQUID JET SCALPEL AND METHOD FOR
OPERATING A LIQUID JET SCALPEL

This application claims priority of German Patent Application No. 10 2011 087 748.7 filed Dec. 5, 2011, which claims priority of U.S. Patent Application No. 61/711,881 filed Oct. 10, 2012, these applications being fully incorporated herewith by reference.

BACKGROUND OF THE INVENTION

1. Field of the Invention

The present invention relates to a liquid jet scalpel and a method for operating a liquid jet scalpel.

2. Description of the Prior Art

Liquid jet scalpels are used in the medical sector, e.g. in water jet surgery.

Water jet surgery, which surgeons tend to use ever more frequently, offers the possibility to sever soft tissue in a selective manner. Thus, for instance, it is rendered possible to sever liver tissue while blood vessels and nerves will be left undamaged. For severing the tissue, a nozzle, discharging water at high pressure, will be moved along the cutting path at a small distance from the surface of the tissue. The soft tissue will be washed off and removed by suction; the blood vessels and the nerves remain undamaged but now form unprotected bridges between the parts of organs which are to be severed. In case that also the nerves and blood vessels shall be severed, this will require an additional working step in which, e.g. with the aid of an additional tool (e.g. electric scalpel or scissors), the remaining strands will be cut off in a well-aimed manner. If blood vessels have to be severed, it is necessitated to interrupt the blood flow (e.g. by use of an electric scalpel or clamps) prior to performing the cutting. As of yet, the entire intervention has been performed exclusively under visual control.

When using a liquid jet scalpel, it may undesirably happen that vessels are damaged by the nozzle or the instrument shaft. In case that these vessels are blood vessels, the resultant bleeding may drastically impair the visibility in the area of the surgical intervention. Further, the bleeding may cause a premature decrease of the blood flow through an organ part that is to be severed.

It is an object of the invention to provide a liquid jet scalpel and a method for operating the same which make it possible to avoid damage to the tissue.

SUMMARY OF THE INVENTION

According to the invention, the above object is achieved by the features defined in device claim 1 and method claim 5.

The liquid jet scalpel of the invention comprises a nozzle for discharge of the pressurized liquid in the direction of the tissue that is to be manipulated. Said liquid can be e.g. water. The liquid jet scalpel of the invention further comprises a distance measuring device for measuring the distance between the nozzle and the to-be-manipulated tissue. This manipulated tissue can be tissue which is to be cut by the liquid jet scalpel. On the other hand, this tissue can be tissue which is to be preserved, i.e. tissue which cannot or must not be cut by the liquid jet scalpel. To be counted among such tissue are nerve strands, blood vessels, cartilage or similar structures.

By the liquid jet scalpel of the invention, it is thus rendered possible to obtain information on the distance of the nozzle from the tissue that is to be manipulated. Particularly, on the basis of this measured distance, the surgeon will be able to avoid an inadvertent perforation of tissue which, due to the selective effect of the liquid jet, is not removed (e.g. blood vessels and nerves). In case that such a perforation threatens to be imminent, a warning message can be output. Further, it is made possible to prevent a certain movement of the liquid jet scalpel. Thus, with the aid of the invention, the safety during operation of the liquid jet scalpel can be improved.

It is preferred that, by the distance measuring device, a distance measuring beam and/or a distance measuring wave will be incoupled into the liquid jet. The distance measuring beam can be a light beam, preferably a laser beam. The distance measuring wave can be e.g. an ultrasonic wave by which the distance between the tissue and the nozzle is measured according to the principle of an ultrasonic device. Thus, the distance measuring device can be an optical or an acoustic distance measuring device. The optical acoustic distance measuring device can be realized e.g. in the form of an interferometer, preferably a laser interferometer.

The above mentioned incoupling of the measuring beam into the liquid jet is to be understood in the sense that the liquid jet is used as a transmission medium. If, for instance, use is made of an acoustic distance measuring device of the type for ultrasonic measurement, the ultrasound requires a transmission medium so as to be able to propagate into the body of a patient. According to the invention, this transmission medium can be the liquid jet itself. In an optical distance measuring device, e.g. of the type for distance measurement by laser, it can be provided that a total reflection of the measuring beam will occur in the liquid jet, so that, also in this regard, the liquid jet is used as a transmission medium for the measuring beam or the measurement wave.

By the above mentioned features, the distance measurement can be performed between the nozzle and exactly that site of the tissue which is manipulated by the liquid jet. Preferably, the distance measurement is performed in a contactless manner. This is to say that, except for the liquid issuing from the nozzle, no mechanical connection exists between the nozzle/the distance measuring device and the tissue.

Further, it is preferred that the liquid jet scalpel comprises a device for detecting the spatial position and orientation of the nozzle. This device can be realized e.g. as a tracking system. Further, the liquid jet scalpel can comprise a computation device for computing a model of the to-be-manipulated tissue, or it can be connected to the computation device in a manner allowing for data transmission. The computation of the model is performed on the basis of the measured distance between the nozzle and the tissue, and of the detected position and orientation of the nozzle. Further, the liquid jet scalpel can comprise a warning device, e.g. an acoustic or optical warning device, for emitting a warning signal in case of falling short of a predetermined distance between the nozzle and the tissue which is to be preserved.

The liquid jet scalpel can comprise any one of the features mentioned in the context of the method for operating a liquid jet scalpel as described hereunder.

The inventive method for operating a liquid jet scalpel comprises the following step:

Measuring the distance between the nozzle of the liquid jet scalpel and the tissue which is to be manipulated.

Preferably, there will be detected the spatial position and orientation of the nozzle, and a model of the to-be-manipulated tissue will be computed on the basis of the measured distance between the nozzle and the tissue, and of the detected position and orientation of the nozzle.

Further, as an additional step, a warning message can be output if the distance between the nozzle and the to-be-manipulated tissue falls short of a predetermined threshold value. Particularly, it can be indicated which part of the liquid jet scalpel has entered a range too close to the tissue. This can be performed e.g. on a display device via which the surgeon controls a telemanipulation robot. For instance, it can be indicated that the liquid jet scalpel has come to close to a critical region by its nozzle, its shaft or another part of it.

Further, it is preferred that the distance between the nozzle and the tissue is measured continuously. The term "continuously" as used herein is intended to include also a measurement at brief intervals of time, e.g. at intervals in the range of split seconds. It is thus safeguarded that, during the surgical operation, the nozzle will at no time advance too close to the tissue that is to be manipulated.

According to a preferred embodiment, the method of the invention is used to generate a model of the tissue which is to be preserved. Due to the selectivity in the cutting performed by use of a liquid jet scalpel, certain kinds of tissue (inter alia blood vessels, nerve strands) will not be cut by the scalpel. It may thus happen that, after repeated movement of the nozzle across a tissue that is to be cut (e.g. liver tissue), the tissue has been cut by the liquid jet and has been washed away whereas e.g. a blood vessel at this site has been left untouched. Thus, by the repeated passes of the liquid jet scalpel across this site, this blood vessel—or, in more general terms, the tissue that is to be preserved—has been exposed because no further tissue is still located around this to-be-preserved tissue. If, now, the distance between the nozzle and the tissue is measured during a renewed pass along the same trajectory, there will be observed a sharp decrease of the measured distance in the area of to-be-preserved tissue and then, past the to-be-preserved tissue, a sharp increase of this distance. In other words, the cut tissue has a larger distance to the nozzle than is the case for the exposed preserved tissue which is located distinctly closer to the nozzle. According to the invention, this sharp decrease of distance can be detected on the basis of the measured distance between the nozzle and the tissue. In dependence on the currently performed operation, a threshold value for this sharp decrease and increase of said distance will be set. In case that the sharp decrease and increase of the distance should exceed this set threshold value, it is assumed for the computation of the model of the tissue that, at this site, there is situated a tissue that is to be preserved, e.g. a blood vessel, which—due to the selectivity in the cutting process performed with the liquid jet scalpel—has not been cut by the latter and thus now forms an exposed bridge of tissue that is to be preserved. This bridge of tissue will then be included into the generated tissue model and can be correspondingly considered in the further course of the operation. At this site, one can also establish a software-based restriction of the moving range of the nozzle in cases where the latter is controlled by a medical robot, thus protecting the exposed tissue bridge.

With the above mentioned method steps, it is also rendered possible to evaluate the width of the detected to-be-preserved tissue to the effect that the tissue will be assumed to be tissue of to-be-preserved category e.g. only in case that the sharp decrease of the distance between the nozzle and the tissue extends along a defined minimum width. Otherwise, a measuring error can be assumed.

In case that e.g. a to-be-preserved blood vessel is detected in the above manner, it is possible to interrupt the cutting process performed with the liquid jet scalpel and to sever this blood vessel by methods known from the state of the art. For this purpose, the blood flow will be interrupted, e.g. by an electric scalpel or clamps, prior to the severing. Subsequently, the to-be-preserved vessel can be severed. This severance of the preserved vessel will then be considered in the generated tissue model, e.g. to the effect that this to-be-preserved tissue as such will be removed again from the tissue model.

According to a preferred embodiment of the method of the invention, the liquid jet scalpel is guided by a robot. In this embodiment, the spatial position and orientation of the nozzle can be computed on the basis of measurement values of sensors of the robot. Thus, for determining the spatial position and orientation of the nozzle, use is made of measurement values which are available anyway, notably from the sensors of the robot arranged e.g. in or on the joints of the robot. It is not necessary anymore to provide an additional sensor or e.g. a separate tracking system.

Further, by guiding the liquid jet scalpel with the aid of a robot, a too close approach of the nozzle to the manipulated tissue can be prevented by a preferably software-based restriction of the moving range of the robot. A too close approach is to be understood as an approach which reduces the distance between the nozzle and the to-be-manipulated tissue below a predetermined threshold value. A software-based restriction of the moving range of the robot is to be understood as a restriction which is not effected by hardware-based restrictions, e.g. restrictions of the pivoting range of joints. Instead, this is an artificially generated restriction which is realized by the control unit of the robot and can be varied or eliminated at any desired time.

The last-described method steps are also of use as a good basis for possible partly or wholly autonomous process steps to be performed by a medical robot.

Apart from its application in the field of medical technology, the liquid jet scalpel of the invention can be applied also in other fields, e.g. in industry, where it is required that a certain minimum distance is maintained to the to-be-manipulated objects.

BRIEF DESCRIPTION OF THE DRAWING

A full and enabling disclosure of the present invention, including the best mode thereof, enabling one of ordinary skill in the art to carry out the invention, is set forth in greater detail in the following description, including reference to the accompanying drawing in which the sole FIGURE shows a schematic view of the liquid jet scalpel of the invention.

DETAILED DESCRIPTION OF A PREFERRED EMBODIMENT

A liquid jet scalpel 10 comprises a nozzle 12 arranged on its distal end. On said distal end of the liquid jet scalpel 10, there is further arranged a distance measuring device 18 oriented e.g. coaxially to the nozzle 12. From the nozzle 12, a water jet 14 is discharged in the direction of the tissue 16 which is to be manipulated. The water jet 14 will impinge onto the tissue 16 at the site 16a. Said distance measuring device 18 emits a distance measuring beam 20, e.g. a laser beam, by which the distance between the nozzle 12 and said spot 16a is measured. This can be performed e.g. by a laser interferometer which is a part of the distance measuring device 18. The laser beam 20 will thus be incident on the tissue 16 substantially at the same spot 16a as the water jet 14.

Although the invention has been described and illustrated with reference to specific illustrative embodiments thereof, it is not intended that the invention be limited to those illustrative embodiments. Those skilled in the art will recognize that variations and modifications can be made without departing from the true scope of the invention as defined by the claims that follow. It is therefore intended to include within the invention all such variations and modifications as fall within the scope of the appended claims and equivalents thereof.

The invention claimed is:

1. A method for operating a liquid jet scalpel, comprising the steps of:
    measuring a distance between a nozzle of the liquid jet scalpel and tissue which is to be manipulated,
    detecting a spatial position and orientation of the nozzle,
    computing a model of the tissue that is to be manipulated on the basis of the measured distance between the nozzle and the tissue that is to be manipulated and of the detected position and orientation of the nozzle;
    when the measured distance between the nozzle and the tissue shows a sharp decrease and a subsequent sharp increase, with said decrease and said increase exceeding a predetermined threshold value, it is assumed for computation of the model of the tissue that, at this site, there is situated a tissue that is to be preserved, which tissue, due to the selectivity in a cutting process performed with the liquid jet scalpel, has not been cut by the scalpel and thus forms an exposed bridge of tissue that is to be preserved, and wherein said bridge of tissue is included into the tissue model.

2. The method according to claim 1, wherein the model of the tissue that is to be manipulated is a model of the tissue that is to be preserved.

3. The method according to claim 1, wherein the following further step is provided:
    issuing a warning message if the distance between the nozzle and the tissue, particularly the tissue that is to be preserved, falls short of a predetermined threshold value.

4. The method according to claim 1, wherein the liquid jet scalpel is guided by a robot and the spatial position and orientation of the nozzle is computed on the basis of measurement values of said robot.

5. The method according to claim 4, wherein an approach of the nozzle to the manipulated tissue to a distance closer than defined by a predetermined threshold value, is prevented by a software-based restriction of a moving range of the robot.

6. The method according to claim 3, further including the step of indicating which part of the liquid jet scalpel has come too close to the tissue.

\* \* \* \* \*